US00PP33380P2

(12) United States Plant Patent
Danziger

(10) Patent No.: US PP33,380 P2
(45) Date of Patent: Aug. 17, 2021

(54) ***PETUNIA* PLANT NAMED 'DPETORFRST'**

(50) Latin Name: *Petunia hybrida*
Varietal Denomination: DPETORFRST

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 16/952,674

(22) Filed: Nov. 19, 2020

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13
CPC ..... A01H 6/824
See application file for complete search history.

*Primary Examiner* — Anne Marie Grunberg
(74) *Attorney, Agent, or Firm* — Cassandra Bright

(57) ABSTRACT

A new and distinct *Petunia* plant named 'DPETORFRST' is disclosed, characterized by abundant, extra-large flowers on well-branched plants with a semi-trailing habit. Flowers are uniquely colored purple-violet with 5 white interior stripes and a thin white floral rim. White coloration is more pronounced in higher temperature and more intense light conditions, while flowers have more purple-violet coloration in cooler, lower light conditions. The new variety is a *Petunia*, normally produced as an outdoor garden or container plant.

4 Drawing Sheets

Latin name of the genus and species: *Petunia hybrida.*
Variety denomination: 'DPETORFRST'.

BACKGROUND OF THE INVENTION

The new *Petunia* cultivar is a product of a planned breeding program conducted by the inventor, Gavriel Danziger in Moshav Mishmar Hashiva, Israel. The objective of the breeding program was to produce new *Petunia* varieties for ornamental purposes. The crossing resulting in this new variety was made during January of 2017.

The seed parent is the unpatented, propriety variety referred to as *Petunia* 'PE-15-9860'. The pollen parent is the unpatented, propriety variety referred to as *Petunia* 'PE-15-9943'. The new variety was discovered in September of 2017 by the inventor in a group of seedlings resulting from the crossing, in a greenhouse in Moshav Mishmar Hashiva, Israel.

Asexual reproduction of the new cultivar 'DPETORFRST' was first performed by terminal vegetative cuttings during September of 2017, at a greenhouse in Moshav Mishmar Hashiva, Israel. Subsequent propagation by vegetative cuttings has shown that the unique features of this cultivar are stable and reproduced true to type in more than 6 successive generations. Date of first sale was Dec. 15, 2019, occurring in the United States. This sale was made directly by the inventor or one who obtained the claimed invention directly or indirectly from the inventor. This sale and all public disclosures made between Dec. 15, 2019 and the filing of this application fall within the exception allowed under 102(b)(1).

SUMMARY OF THE INVENTION

The cultivar 'DPETORFRST' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPETORFRST' These characteristics in combination distinguish 'DPETORFRST' as a new and distinct *Petunia* cultivar:

1. Semi-trailing growth habit.
2. Well-branched plant with strong vigor.
3. Flowers uniquely colored purple-violet with 5 white interior stripes and a thin white floral rim. Light intensity and heat influence the width of the stripes, flowers have overall more purple-violet coloration and less white when temperature and light intensity drop; when temperatures and light intensity increase, the white stripes and rim are significantly larger.
4. Extra-large flowers.
5. Abundant flowering.

PARENT COMPARISON

Plants of the new cultivar 'DPETORFRST' are similar to plants of the seed parent in most horticultural characteristics, however, plants of the new cultivar 'DPETORFRST' differ in the following;

1. Plant habit of the new variety is semi-trailing; the seed parent is a mounding plant.
2. The new variety has better vigor and more branches than the seed parent.
3. The new variety has larger flowers than the seed parent.
4. The new variety produces more flowers than the seed parent.

5. Flower color of the new variety is purple-violet with white stripes and margins, flower color of the seed parent is blue with white stripes.

Plants of the new cultivar 'DPETORFRST' are similar to plants of the pollen parent in most horticultural characteristics, however, plants of the new cultivar 'DPETORFRST' differ in the following;

1. Plant habit of the new variety is semi-trailing; the pollen parent is a trailing plant.
2. The new variety produces more branches than the pollen parent.
3. The new variety has larger flowers than the pollen parent.
4. The new variety produces more flowers than the pollen parent.
5. Flower color of the new variety is purple-violet with white stripes and margins, flower color of the pollen parent is light purple with white stripes.

COMMERCIAL COMPARISON

Plants of the new cultivar 'DPETORFRST' can be compared to the commercial variety *Petunia* Cascadias 'Purple Gem', unpatented. These varieties are similar in most horticultural characteristics; however, 'DPETORFRST' differs in the following:

1. Flower color of this comparator is violet-blue with white stripes and rim, while the new variety has purple-violet flowers with white stripes and rim.
2. The new variety produces larger flowers than this comparator.
3. Plants of the new variety are more vigorous than plants of this comparator.

Plants of the new cultivar 'DPETORFRST' can also be compared to the patented commercial variety *Petunia* 'DRAY67' U.S. Plant Pat. No. 25,906. These varieties are similar in most horticultural characteristics; however, 'DPETORFRST' differs in the following:

1. Flowers of the new variety are larger than flowers of this comparator.
2. Flower color of the comparison variety is violet with purple veins, while the new variety has purple-violet flowers with white stripes and rim.
3. Plant form of the new variety is semi-trailing; plant form of this comparator is mounding.

BRIEF DESCRIPTION OF THE PHOTOGRAPHS

The accompanying photograph in FIG. 1 illustrates in full color a typical plant of 'DPETORFRST' grown in a 13 cm pot in Moshav Mishmar Hashiva, Israel under moderate Fall conditions.

Figure 1:
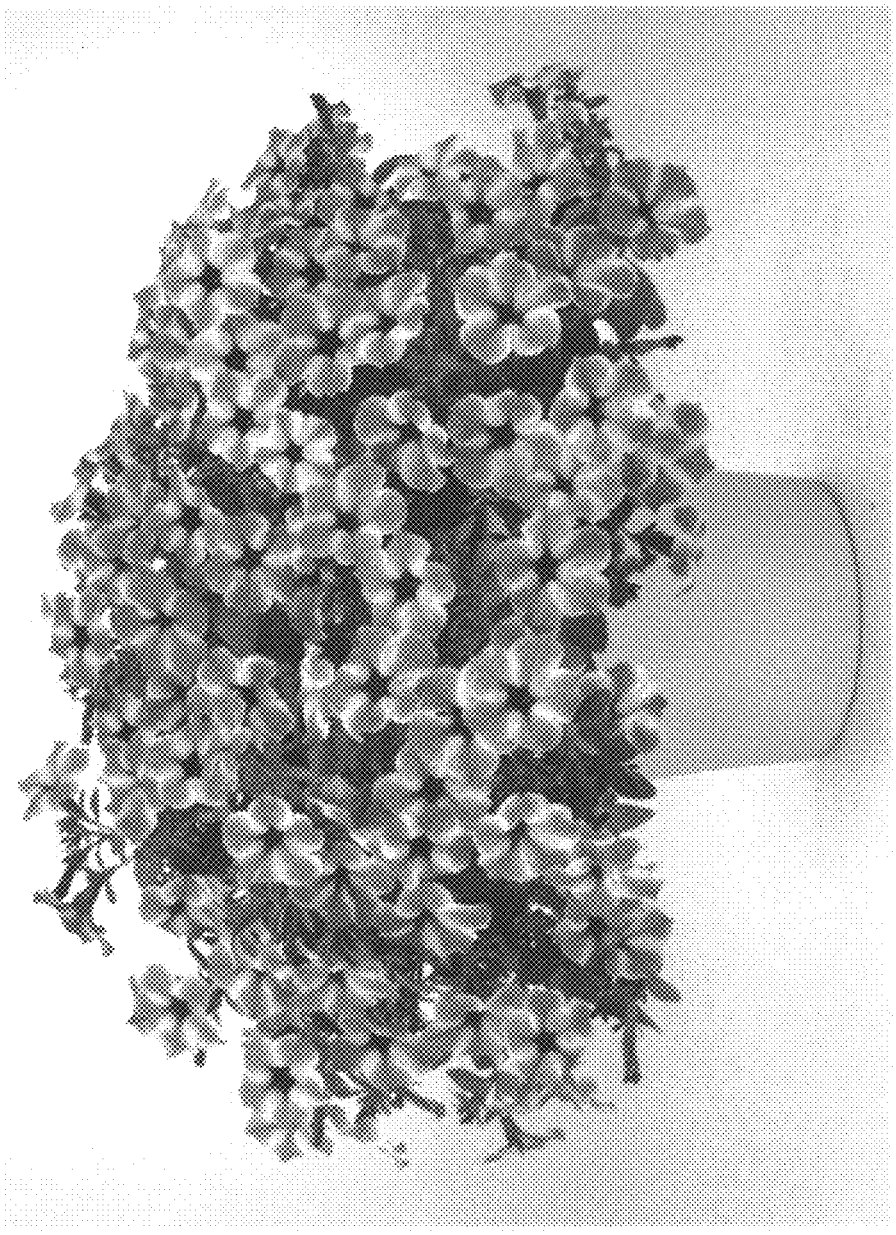
Figure 2:
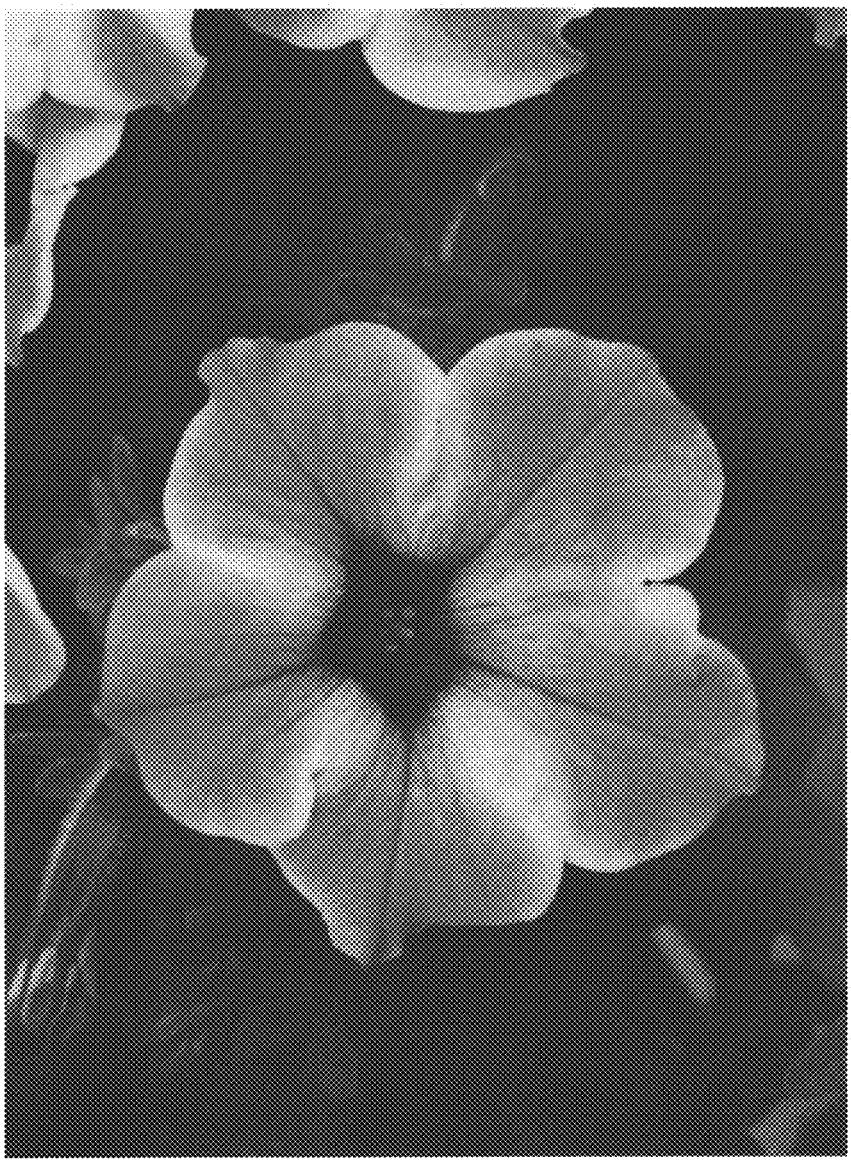
FIG. 2 illustrates in full color a close up view of a typical flower of 'DPETORFRST' grown under the same moderate Fall conditions. Age of the plant photographed is approximately 11 weeks from a rooted cutting in a 13 cm pot.
Figure 3:
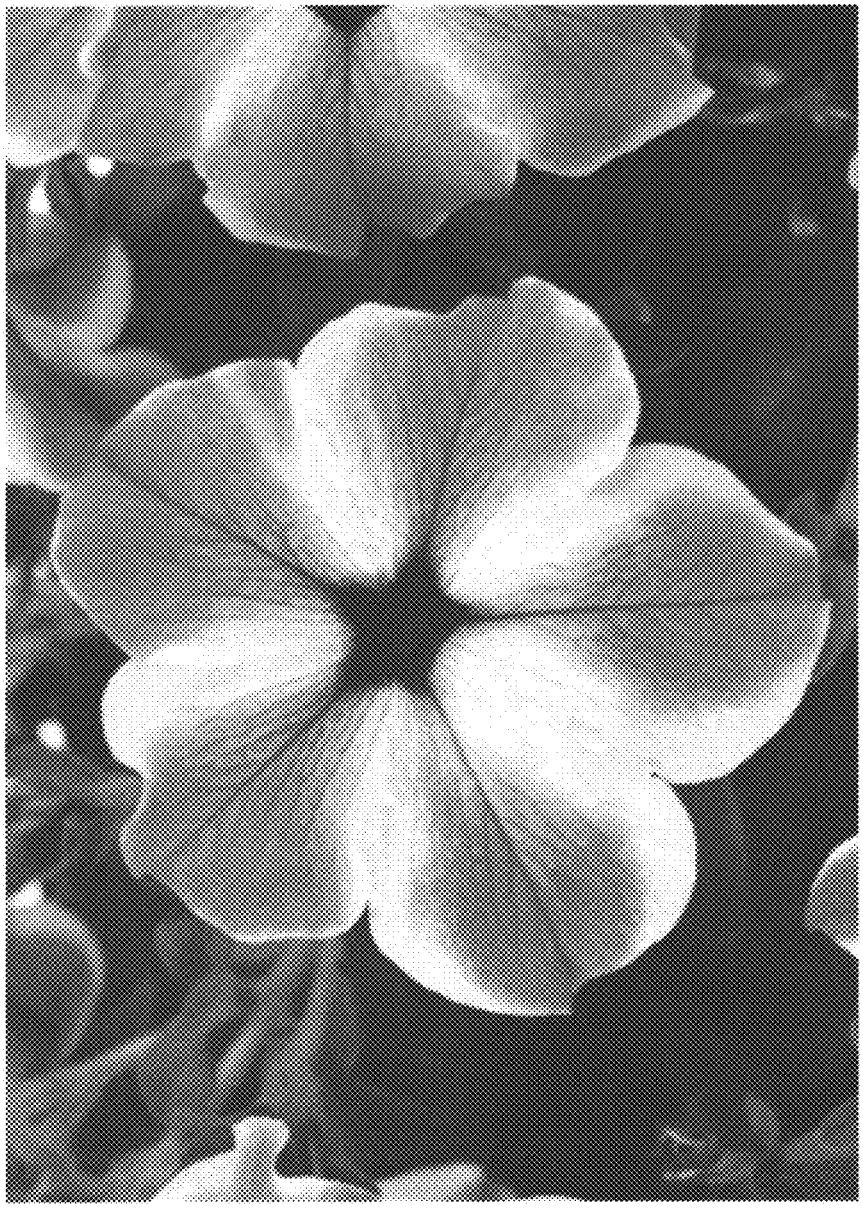
FIG. 3 illustrates in full color a close up view of a typical flower of 'DPETORFRST' grown under high light, high temperature conditions.
Figure 4:
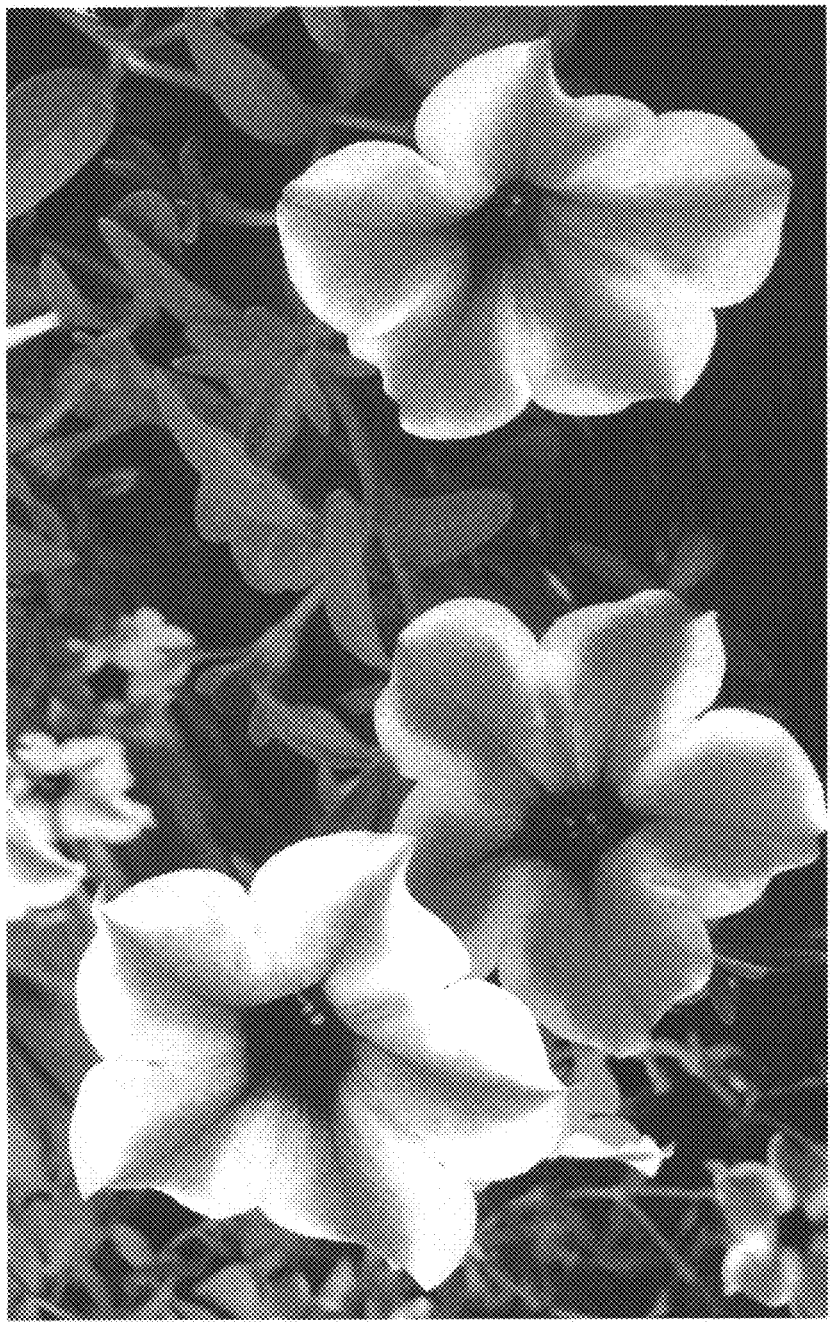
FIG. 4 illustrates multiple flowers on a plant grown under high light, high temperature conditions.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPETORFRST' plants grown in a greenhouse in Moshav Mishmar Hashiva, Israel, under natural lighting. Measurements were taken during Summer of 2020. The plants were approximately 60 days old from a rooted cutting in a 12 cm pot. The growing temperature ranged from approximately 18° C. to 28° C. during the days, 13° C. to 18° C. during the nights. Measurements and numerical values represent averages of typical plant types. Measurements taken during June of 2020.

Botanical classification: *Petunia hybrida* 'DPETORFRST'.

PROPAGATION

Total rooting time: About 10 to 14 days at approximately 20° C.

Root description: Fibrous and white, color not accurately measured with R.H.S. chart.

PLANT

Growth habit: Semi-trailing.
Pot size of plant described: 13 cm.
Height: To top of flowers: about 20 cm.
Plant spread: about 70 cm.
Growth rate: Vigorous.
Branching characteristics:
Length of primary lateral branches: About 35 cm.
Diameter of lateral branches: About 0.3 cm.
Quantity of primary lateral branches: 8.
Characteristics of primary lateral branches:
*Form*.—Cylindrical.
*Diameter*.—About 0.3 cm.
*Color*.—RHS Yellow-Green 144 B.
*Texture*.—Pubescent.
*Strength*.—Strong.
Internode length: About 2.5 cm.

FOLIAGE

Leaf:
*Arrangement*.—Opposite.
*Quantity*.—Approximately 40 per branch.
*Average length*.—7 cm.
*Average width*.—3 cm.
*Shape of blade*.—Elliptic.
*Apex*.—Obtuse.
*Base*.—Acute.
*Margin*.—Entire.
*Texture of top surface*.—Velvety.
*Texture of bottom surface*.—Velvety.
*Angle of attachment*.—90 degrees.
*Color*.—Young foliage upper side: RHS Green 137 C. Young foliage under side: RHS Yellow-Green 146 B. Mature foliage upper side: RHS Green N 137 A. Mature foliage under side: RHS Yellow-Green 146 B. Venation: Type: Pinnate. Venation color upper side: RHS Yellow-Green 146 B. Venation color under side: RHS Yellow-Green 146 C. Petiole: Length: about 0.8 cm. Diameter: about 0.3 cm. Color: RHS Yellow-Green 146 B. Texture: Velvety.

FLOWER

Bloom period: In moderate climate zones, USDA Zone 7 and up blooming occurs from Spring to late Fall.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3-6 days.
Approximate quantity of flowers per plant: About 60.
Persistent or self-cleaning: Self-cleaning.
Bud:
*Shape*.—Tubular.
*Length*.—About 5 cm.
*Diameter*.—About 1 cm.
*Color*.—RHS Violet 83 A.
Flower size:
*Diameter*.—About 7.5 cm.
*Flower tube length*.—About 3 cm.
*Flower tube diameter at distal end*.—About 1.5 cm.
*Flower tube diameter at proximal end*.—About 0.4 cm.
Petals:
*Length from throat*.—About 3 cm.
*Width*.—About 3 cm.
*Quantity*.—5.
*Texture*.—Velvety.
*Apex*.—Acute.
*Margin*.—Entire.
Color:
When opening:
*Upper surface*.—RHS Purple-Violet N 80 A with 5 Stripes and rim, White NN 155 D.
*Lower surface*.—RHS Purple-Violet N 80 C with 5 Stripes and rim, White NN 155 D.
Fully opened:
*Upper surface*.—RHS Purple-Violet N 80 B with 5 Stripes and rim, White NN 155 D. White stripes and rim significantly thicker during hot temperatures.
*Lower surface*.—RHS Purple-Violet N 80 D with 5 Stripes and rim, White NN 155 D.
*Flower throat* (*inside*).—RHS Purple-Violet N 80 B.
*Flower throat, vein*.—RHS Violet-Blue N 92 C (dense veins at opening).
*Flower tube* (*outside*).—RHS Purple-Violet N 81 A.
*Flower tube, vein*.—RHS Yellow-Green N 144 D.
Fading:
*Petals fading to*.—RHS Purple-Violet N 80 C with 5 Stripes and rim, White NN 155 D The White stripes and rim are usually wider at this stage.
Calyx/sepals:
*Quantity per flower*.—5.
*Shape*.—Linear.
*Length*.—About 1.5 cm.
*Width*.—About 0.5 cm.
*Apex*.—Obtuse.
*Base*.—Cuneate.
*Margin*.—Entire.
*Texture*.—Velvety.
*Color*.—Upper Surface: RHS Green 137 C.
*Lower surface*.—RHS Yellow-Green 146 B.
Pedicel:
*Length*.—About 2 cm.
*Diameter*.—About 0.2 cm.
*Color*.—RHS Yellow-Green 146 C.
*Orientation*.—45 degrees.
Fragrance: None.

REPRODUCTIVE ORGANS

Stamens:
*Number*.—5.
*Filament length*.—About 2 cm.
Anthers:
*Length*.—About 0.2 cm.
*Shape*.—Rounded.
*Color*.—RHS Violet 85 C.
*Pollen*.—
*Color*.—RHS Violet-Blue 92 B. Quantity: Plenty.
Pistil:
*Number*.—1.
*Length*.—About 2.8 cm.
*Style*.—Length: about 2.3 cm. Color: RHS Yellow-Green N 144 D.
*Stigma*.—Shape: Rounded. Color: RHS Yellow-Green 144 C. Ovary Color: RHS Yellow-Green 146 C.

OTHER CHARACTERISTICS

Seeds and fruits: About 80 dark brown, rounded seeds of about 0.5 mm diameter, per one, conical capsule. Colored near Brown 200B.
Disease/pest resistance: Neither resistance nor susceptibility to the normal diseases and pests of *Petunia* have been observed. Pests common to *Petunia* include Aphids and thrips. Typical diseases are *Botrytis* and *Pythium*.
Temperature tolerance: Tolerates a range between 5° C. to 40° C.

What is claimed is:

1. A new and distinct cultivar of *Petunia* plant named 'DPETORFRST' as herein illustrated and described.

* * * * *